(12) United States Patent
Vanasse et al.

(10) Patent No.: US 8,506,638 B2
(45) Date of Patent: Aug. 13, 2013

(54) SHOULDER PROSTHESIS

(75) Inventors: Thomas M. Vanasse, Warsaw, IN (US); Nathan A. Winslow, Warsaw, IN (US)

(73) Assignee: Biomets Manufacturing, LLC, Warsaw, IN (US)

( * ) Notice: Subject to any disclaimer, the term of this patent is extended or adjusted under 35 U.S.C. 154(b) by 58 days.

(21) Appl. No.: 13/182,026

(22) Filed: Jul. 13, 2011

(65) Prior Publication Data

US 2013/0018475 A1 Jan. 17, 2013

(51) Int. Cl.
*A61F 2/40* (2006.01)

(52) U.S. Cl.
USPC ................................ 623/19.14; 623/19.11

(58) Field of Classification Search
USPC .......................................... 623/19.14, 22.23
See application file for complete search history.

(56) References Cited

U.S. PATENT DOCUMENTS

| | | | |
|---|---|---|---|
| 3,803,641 A | 4/1974 | Golyakhovsky et al. |
| 3,916,451 A | 11/1975 | Buechel et al. |
| 3,979,778 A | 9/1976 | Stroot |
| 4,042,980 A | 8/1977 | Swanson et al. |
| 4,045,825 A | 9/1977 | Stroot |
| 4,045,826 A | 9/1977 | Stroot |
| 4,206,517 A | 6/1980 | Pappas et al. |
| 4,355,429 A | 10/1982 | Mittelmeier et al. |
| 4,550,450 A | 11/1985 | Kinnett |
| D285,968 S | 9/1986 | Kinnett |
| 4,624,673 A | 11/1986 | Meyer |
| 4,725,280 A | 2/1988 | Laure |
| D295,076 S | 4/1988 | Homsy et al. |
| 4,865,605 A | 9/1989 | Dines et al. |
| 4,883,491 A | 11/1989 | Mallory et al. |
| 4,919,669 A | 4/1990 | Lannelongue et al. |
| 4,964,865 A | 10/1990 | Burkhead et al. |
| 4,964,867 A | 10/1990 | Boger |
| 4,986,833 A | 1/1991 | Worland |
| 5,030,219 A | 7/1991 | Matsen, III et al. |
| 5,032,132 A | 7/1991 | Matsen, III et al. |
| 5,080,673 A | 1/1992 | Burkhead et al. |
| 5,108,446 A | 4/1992 | Wagner et al. |
| 5,326,366 A | 7/1994 | Pascarella et al. |
| 5,360,452 A | 11/1994 | Engelhardt et al. |
| 5,437,677 A | 8/1995 | Shearer et al. |

(Continued)

FOREIGN PATENT DOCUMENTS

| DE | 2041929 A1 | 3/1971 |
|---|---|---|
| EP | 1520560 A1 | 4/2005 |

(Continued)

OTHER PUBLICATIONS

International Search Report for International Application No. PCT/US2012/040340, dated Aug. 17, 2012.

(Continued)

*Primary Examiner* — Thomas J Sweet
*Assistant Examiner* — Brian Dukert
(74) *Attorney, Agent, or Firm* — Harness, Dickey

(57) ABSTRACT

A prosthesis is provided and may include a central body having a longitudinal axis and a plurality of arms extending from the central body in a direction substantially perpendicular to the longitudinal axis. The plurality of arms may each include a first planar surface, a second planar surface, and a third planar surface that are each formed at an obtuse angle relative to one another to define an outer shape of the prosthesis.

14 Claims, 10 Drawing Sheets

(56) References Cited

U.S. PATENT DOCUMENTS

| | | | |
|---|---|---|---|
| 5,489,309 | A | 2/1996 | Lackey et al. |
| 5,489,310 | A | 2/1996 | Mikhail |
| 5,507,819 | A | 4/1996 | Wolf |
| 5,512,145 | A | 4/1996 | Hollenberg |
| 5,549,691 | A | 8/1996 | Harwin |
| 5,593,448 | A | 1/1997 | Dong |
| 5,702,447 | A | 12/1997 | Walch et al. |
| 5,725,592 | A | 3/1998 | White et al. |
| 6,102,951 | A | 8/2000 | Sutter et al. |
| 6,228,119 | B1 | 5/2001 | Ondrla et al. |
| 6,245,074 | B1 | 6/2001 | Allard et al. |
| 6,277,390 | B1 | 8/2001 | Schaffner |
| 6,364,910 | B1 | 4/2002 | Shultz et al. |
| 6,379,386 | B1 | 4/2002 | Resch et al. |
| 6,406,495 | B1 | 6/2002 | Schoch |
| 6,448,315 | B1 | 9/2002 | Lidgren et al. |
| 6,506,214 | B1 | 1/2003 | Gross |
| 6,506,216 | B1 | 1/2003 | McCue et al. |
| 6,514,287 | B2 | 2/2003 | Ondrla et al. |
| 6,673,115 | B2 | 1/2004 | Resch et al. |
| 6,699,289 | B2 | 3/2004 | Iannotti et al. |
| 6,761,740 | B2 | 7/2004 | Tornier et al. |
| 6,875,234 | B2 | 4/2005 | Lipman et al. |
| 6,896,703 | B2 * | 5/2005 | Barbieri et al. ............... 623/22.3 |
| 6,911,047 | B2 | 6/2005 | Rockwood, Jr. et al. |
| 6,942,699 | B2 | 9/2005 | Stone et al. |
| 7,160,328 | B2 | 1/2007 | Rockwood, Jr. et al. |
| 7,204,854 | B2 | 4/2007 | Guederian et al. |
| 7,214,764 | B2 | 5/2007 | King |
| 7,303,585 | B2 | 12/2007 | Horber |
| 7,431,874 | B2 | 10/2008 | Muratoglu et al. |
| 7,445,638 | B2 | 11/2008 | Beguin et al. |
| 7,498,365 | B2 | 3/2009 | Muratoglu et al. |
| 7,753,959 | B2 | 7/2010 | Berelsman et al. |
| 2001/0011192 | A1 | 8/2001 | Ondrla et al. |
| 2001/0037153 | A1 | 11/2001 | Rockwood et al. |
| 2001/0047210 | A1 | 11/2001 | Wolf |
| 2002/0063552 | A1 | 5/2002 | Arakawa |
| 2002/0082702 | A1 | 6/2002 | Resch et al. |
| 2003/0055507 | A1 | 3/2003 | McDevitt et al. |
| 2003/0125809 | A1 | 7/2003 | Iannotti et al. |
| 2003/0158605 | A1 | 8/2003 | Tornier |
| 2003/0216813 | A1 | 11/2003 | Ball et al. |
| 2004/0030396 | A1 | 2/2004 | Horber |
| 2004/0059424 | A1 | 3/2004 | Guederian et al. |
| 2004/0122519 | A1 | 6/2004 | Wiley et al. |
| 2004/0122520 | A1 | 6/2004 | Lipman et al. |
| 2004/0193276 | A1 | 9/2004 | Maroney et al. |
| 2004/0225367 | A1 | 11/2004 | Glien et al. |
| 2004/0230197 | A1 | 11/2004 | Tornier et al. |
| 2005/0049709 | A1 | 3/2005 | Tornier |
| 2005/0060039 | A1 | 3/2005 | Cyprien |
| 2005/0209700 | A1 | 9/2005 | Rockwood et al. |
| 2005/0246028 | A1 | 11/2005 | Pappas et al. |
| 2005/0261775 | A1 | 11/2005 | Baum et al. |
| 2006/0065302 | A1 | 3/2006 | Gibson et al. |
| 2006/0149387 | A1 | 7/2006 | Smith et al. |
| 2006/0155383 | A1 | 7/2006 | Smith et al. |
| 2007/0142914 | A1 | 6/2007 | Jones et al. |
| 2007/0162147 | A1 | 7/2007 | Lewis et al. |
| 2007/0219637 | A1 | 9/2007 | Berelsman et al. |
| 2009/0062923 | A1 | 3/2009 | Swanson |
| 2009/0143865 | A1 | 6/2009 | Hassler et al. |
| 2010/0114326 | A1 | 5/2010 | Winslow et al. |
| 2010/0274359 | A1 * | 10/2010 | Brunnarius et al. ....... 623/19.13 |

FOREIGN PATENT DOCUMENTS

| | | |
|---|---|---|
| EP | 1639967 A1 | 3/2006 |
| EP | 2243444 A1 | 10/2010 |
| FR | 2377798 A2 | 8/1978 |
| FR | 2418644 A1 | 9/1979 |
| FR | 2674122 A1 | 9/1992 |
| FR | 2860425 A1 | 4/2005 |
| WO | 0239933 A1 | 5/2002 |
| WO | 03/051238 A1 | 6/2003 |
| WO | 2008/146124 A2 | 12/2008 |
| WO | 2011/081797 A1 | 7/2011 |

OTHER PUBLICATIONS

Written Opinion of the International Searching Authority for International Application No. PCT/US2012/040340, dated Aug. 17, 2012.

T.E.S.S. á Shoulder System Surgical Technique, BIOMET France SARL, Aug. 2008.

Zatsepin S.T., Burdygin V.N.. Total endoprosthesis of the humerus in tumors thereof and late results. Ortopediya, travmatologiya I protezirovaniye (Orthopedics, traumatology and prosthesis). Kharkov, 1993, No. 1, pp. 14-16.

Goguadze D.M.. Endoprosthesis of the femur and the humerus head with corundum-ceramic prostheses in traumatic injuries in elderly and senile patients. Auto-thesis of the Doctor of Medical Sciences Degree dissertation, Tbilisi, 1933.

Pal'shin G.A.. Total endoprosthesis of the femur and the humerus in extensive lesion thereof by primary tumors and tumor-like diseases in adults. The Doctor of Medical Sciences dissertation, Moscow, 1998. Total endoprosthesis in sparing operations in patients with primary tumors of the femur and the humerus. A manual for physicians. Moscow, 2001.

Pal'shin G.A. Humeral extirpation with endoprosthesis in a total or subtotal lesion thereof by tumors and tumor-like diseases as an alternative to crippling operations. Vestnik travmatologii i ortopedir im. Priorova N.N. (The Herald of Traumatology and Orthopedics named after Priorov N.N.), Moscow, 1998, No. 1, pp. 24-27.

Khamraev Sh.Sh., Khudajbergenov A.A. Experience with endoprosthesis in tumors of the proximal humerus. Vestnik travmatologii i ortopedii' im. Priorova N.N. (The Herald of Traumatology and Orthopedics named after Priorov n. N.), Moscow, 1996, No. 2, pp. 61-62.

Kishko A.I., Humeral endoprosthesis. The Doctor of Medical Sciences dissertation, Sankt-Peresburg, 1999.

"Anchor Peg Glenoid, Desig Rationale & Surgical Technique," copyright 2002, DePuy Orthopaedics Inc. (10 pgs).

"Cementless Surface Replacement Arthroplasty of the Shoulder 5- to 10-year Results with the Copeland Mark-2 Prosthesis;" Levy, O & S.A. Copeland, J. Bone Joint Surg Brochure, p. 213-21, vol. 83B, No. 2, Mar. 2001.

"Cementless Total Shoulder Replacement," S. Copeland, pp. 289-293, Surgery of the Shoulder, Edited by M. Post, B. F. Morrey, and R. J. Hawkins, St. Louis, Mosby-Year Book, 1990.

"Comprehensive Shoulder System Surgical Technique," Biomet Orthopedics, 2007, pp. 1-53.

"Copeland/Copeland EAS Humeral Resurfacing Head Surgical Technique," Biomet, 2008, pp. 1-24.

"Resurfacing Arthroplasty of the Shoulder," Copeland, et al., Techniques in Shoulder and Elbow Surgery, pp. 199-210, vol. 4, Issue 4, copyright 2003 Lippincott, Williams & Wilkins Inc.

"Surface Replacement Arthroplasty of the Shoulder," by S. Copeland, et al., article, pp. 1-19, www.readingsshoulderunit.com, Journal of Current Orthopaedics 2002, vol. 16, part 1.

"The Cofield Total Shoulder System," 1989, by Richards Medical Co. (5 pgs).

Final Office Action for U.S. Appl. No. 11/385,035, mailed Jun. 16, 2008.

Final Office Action for U.S. Appl. No. 11/385,035, mailed May 19, 2009.

Non-Final Office Action for U.S. Appl. No. 11/385,035, mailed Dec. 12, 2008.

Non-Final Office Action for U.S. Appl. No. 11/385,035, mailed Oct. 17, 2007.

Non-Final Office Action for U.S. Appl. No. 11/385,035, mailed Sep. 15, 2009.

Non-Final Office Action for U.S. Appl. No. 13/343,039, mailed Jan. 16, 2013.

International Search Report and Written Opinion of the International Searching Authority regarding International Application No. PCT/US20121069720, dated Feb. 15, 2013.

* cited by examiner

SHOULDER PROSTHESIS

FIELD

The present disclosure relates to a shoulder prosthesis and more particularly to a shoulder prosthesis having a stemless humeral component.

BACKGROUND

This section provides background information related to the present disclosure which is not necessarily prior art.

The shoulder joint includes the humerus, the clavicle, and the scapula, which cooperate to afford a range of motion of the humerus relative to the scapula and clavicle during arm movement. Specifically, a proximal end of the humerus is disposed adjacent to the glenoid fossa of the scapula and is permitted to move relative to the glenoid fossa to provide a range of motion to the humerus relative to the scapula.

Joint replacement surgery such as a partial or total shoulder arthroplasty may be required when the shoulder joint causes pain during use or is otherwise damaged. For example, the shoulder joint may be damaged due to osteoarthritis, whereby progressive wearing away of cartilage results in bare bone being exposed within the shoulder joint. Under such circumstances, it is often necessary to undergo a partial or total shoulder arthroplasty in order to relieve pain and increase the range of motion of the humerus by rebuilding portions of the shoulder joint.

In performing a total shoulder arthroplasty, a surgeon resects a portion of the proximal end of the humerus that is received by the glenoid fossa. Once the distal end of the humerus is resected, the surgeon may then ream the humerus to access the humeral canal. Providing access to the humeral canal allows the surgeon to insert a humeral component into the humeral canal. A prosthetic hemispherical humeral head may then be attached to a proximal end of the humeral component such that the resected portion of the humerus is replaced by the prosthetic hemispherical humeral head. If necessary, the surgeon will likewise replace a portion of the glenoid fossa to provide a bearing surface against which the humeral head may articulate. Upon completion of the shoulder arthroplasty, pain is typically alleviated and the patient is provided with an increased range of motion at the shoulder joint.

While conventional shoulder prosthetics used during shoulder arthroplasty adequately provide the patient with an increased range of motion, conventional shoulder prosthetics require insertion of a stem into the humeral canal of the humerus, thereby increasing the overall weight, size, and cost of the humeral component. Furthermore, because the surgeon is required to insert the stem of the humeral component into the humeral canal, the surgical procedure is somewhat complex, as the surgeon is first required to resect the proximal end of the humerus and subsequently ream the humeral canal prior to inserting the stem of the humeral component into the humeral canal. Increasing the complexity of the joint-replacement surgery increases the time in which the surgeon must spend in performing the procedure and therefore increases the overall cost of the procedure. Finally, requiring insertion of the stem into the humeral component results in additional bone removal, thereby increasing trauma and post-operative pain.

SUMMARY

This section provides a general summary of the disclosure, and is not a comprehensive disclosure of its full scope or all of its features.

A prosthesis is provided and may include a central body having a longitudinal axis and a plurality of arms extending from the central body in a direction substantially perpendicular to the longitudinal axis. The plurality of arms may each include a first planar surface, a second planar surface, and a third planar surface that are each formed at an obtuse angle relative to one another to define an outer shape of the prosthesis.

In another configuration, a prosthesis is provided and may include a central body having a longitudinal axis and a plurality of arms extending from the central body in a direction substantially perpendicular to the longitudinal axis. The plurality of arms may each include a first planar surface, a second planar surface, and a third planar surface that are each formed at an obtuse angle relative to one another and at an acute angle relative to the longitudinal axis to define an outer shape of the prosthesis.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figures 25, 26, 27:
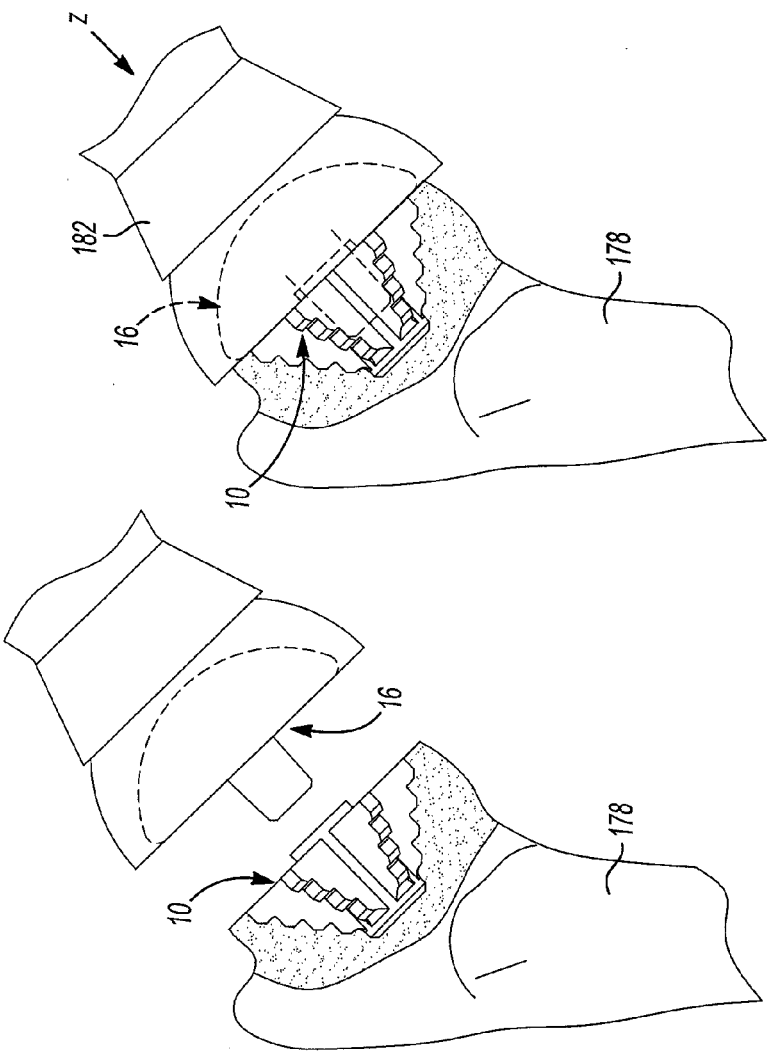
FIG. 25 is a partial perspective view of a proximal end of the humerus showing a line of resection.

FIG. 26 is a partial side view of the humerus with a portion of the bone removed to show a humeral component of a shoulder prosthesis in accordance with the principles of the present disclosure received within a resected portion of the humerus; and FIG. 27 is a partial side view of the humerus with a portion of the bone removed to show a humeral component of a shoulder prosthesis in accordance with the principles of the present disclosure being inserted therein.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 1:
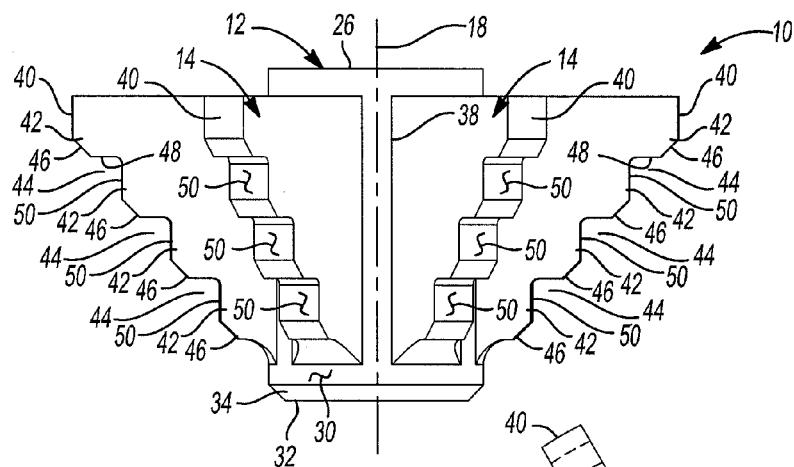
FIG. 1 is a side view of a humeral component of a shoulder prosthesis in accordance with the principles of the present disclosure.
Figure 2:
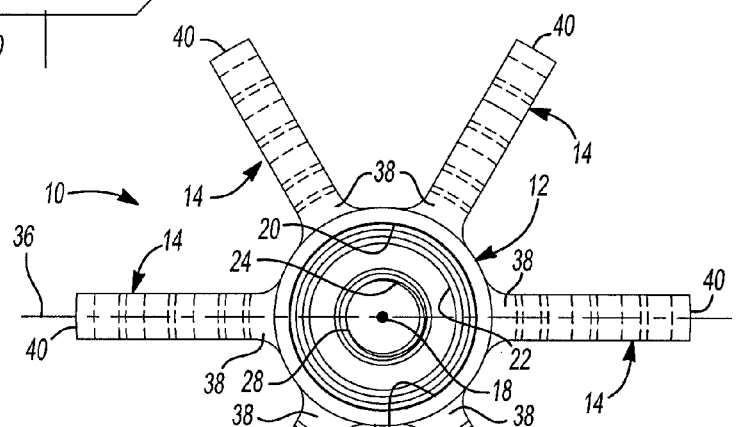
FIG. 2 is a top view of the humeral component of FIG. 1.
Figure 3:
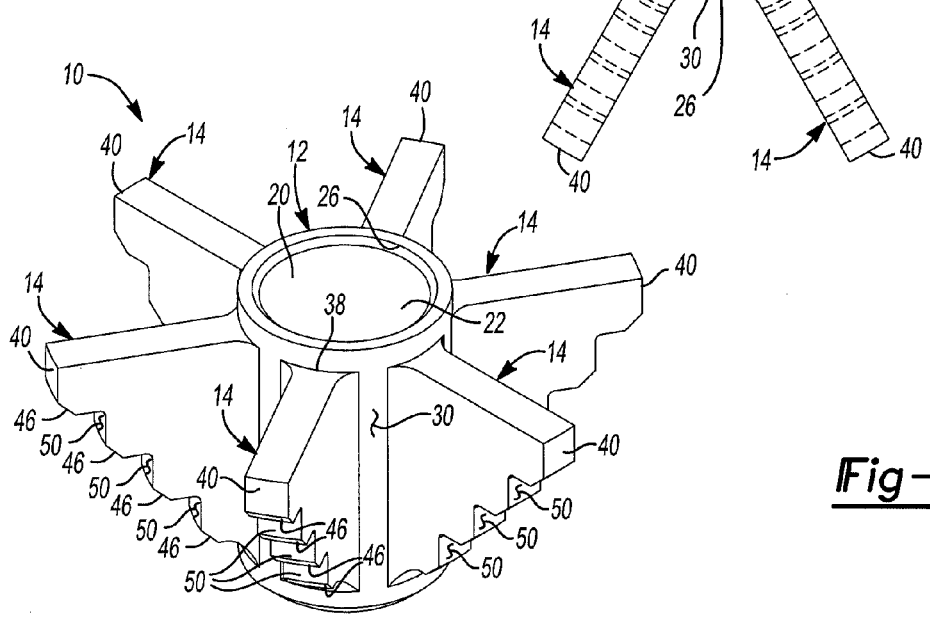
FIG. 3 is a perspective view of the humeral component of FIG. 1.
Figure 23:
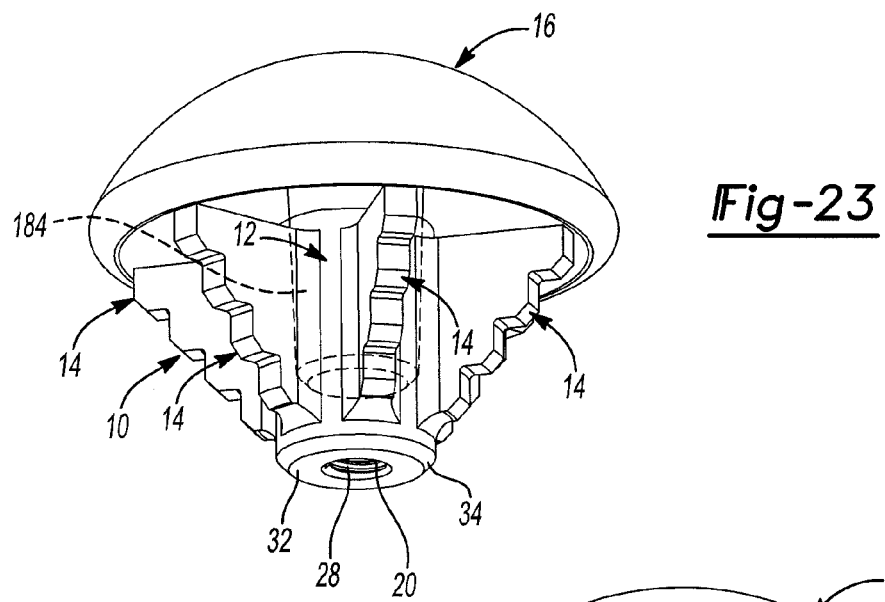
FIG. 23 is a perspective view of a humeral component of a shoulder prosthesis in accordance with the principles of the present disclosure receiving a humeral head.
Figure 24:
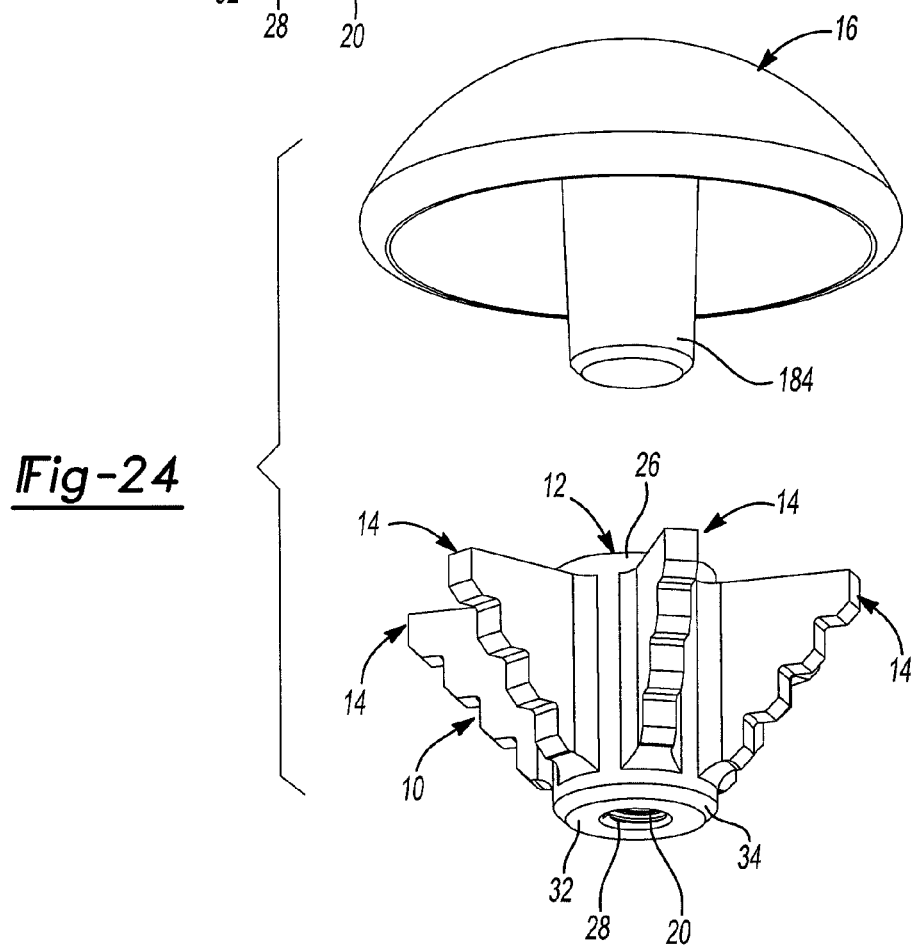
FIG. 24 is an exploded view of the humeral component and humeral head of FIG. 23.

With particular reference to FIGS. 1-3, a prosthesis 10 is provided and may include a central body 12 and a plurality of wings or arms 14 extending generally from the central body 12. The prosthesis 10 may be received within a resected humeral head (FIGS. 26, 27) and may provide the resected humerus with a structure to support a prosthetic humeral head 16 (FIGS. 23, 24). The prosthetic humeral head 16 may be received by the prosthesis 10 once the prosthesis 10 is installed in the resected humerus during a partial or total shoulder arthroplasty or, alternatively, may be received by the prosthesis 10 prior to insertion of the prosthesis 10 into the proximal humerus.

The central body 12 may include a substantially cylindrical shape having a longitudinal axis 18 and a bore 20 at least partially formed therein. The bore 20 may be substantially circular and may include a central axis that is aligned with the longitudinal axis 18 and may include a first portion 22 and a second portion 24. The first portion 22 is disposed proximate to an opening 26 of the central body 12 and may include a Morse taper. The second portion 24 is disposed generally adjacent to the first portion 22 and may include a smaller diameter than the first portion 22. The second portion 24 may include a series of threads 28 (FIG. 2) for use during installation or removal of the prosthesis 10 from the humerus. The bore 20 may extend completely through the central body 12 and along the longitudinal axis 18 or, alternatively, may be a blind bore. Regardless of the particular construction of the bore 20, the first portion 22 is in fluid communication with the second portion 24 such that access to the second portion 24 is obtained via the first portion 22 at the opening 26 of the central body 12.

The central body 12 may include a substantially uniform outer surface 30 and a distal end 32 having a radiused, beveled, or chamfered outer edge 34. The radiused or beveled outer edge 34 may be positioned at the distal end 32 to facilitate insertion of the distal end 32 into a resected end of the humerus during installation (FIGS. 26, 27).

The arms 14 extend generally away from the central body 12 in a direction substantially perpendicular to the longitudinal axis 18. The arms 14 may be positioned relative to the central body 12 such that an imaginary line 36 bisecting the central body 12 in a direction substantially perpendicular to the longitudinal axis 18 of the central body 12 extends through a pair of the arms 14 (FIG. 2). In one configuration, the plurality of arms 14 may include six arms such that three such lines 36 may intersect the longitudinal axis 18 while concurrently passing through respective pairs of the six arms 14.

Each arm 14 may be integrally formed with the central body 12 and may include a first end 38 disposed at a junction of each arm 14 and the central body 12 and a second end 40 formed at an opposite end of each arm 14 from the first end 38. The first end 38 may be tapered to increase the overall width of each arm 14 at the junction of each arm 14 and the central body 12. Increasing the width of each arm 14 at a junction of the central body 12 and each arm 14 increases the strength of the arms at the junction between the arms 14 and the central body 12, thereby increasing the overall strength of each arm 14 and the connection of each arm 14 to the central body 12.

The second end 40 of each arm 14 may include a series of alternating peaks 42 and valleys 44, as shown in FIG. 1. The peaks 42 may be truncated such that each peak 42 terminates at a substantially planar surface 46. The valleys 44 may be positioned such that each valley 44 is defined by a first surface 48 that is substantially perpendicular to the longitudinal axis 18 of the central body 12 and a second surface 50 that is substantially parallel to the longitudinal axis 18 of the central body 12.

Figure 4:
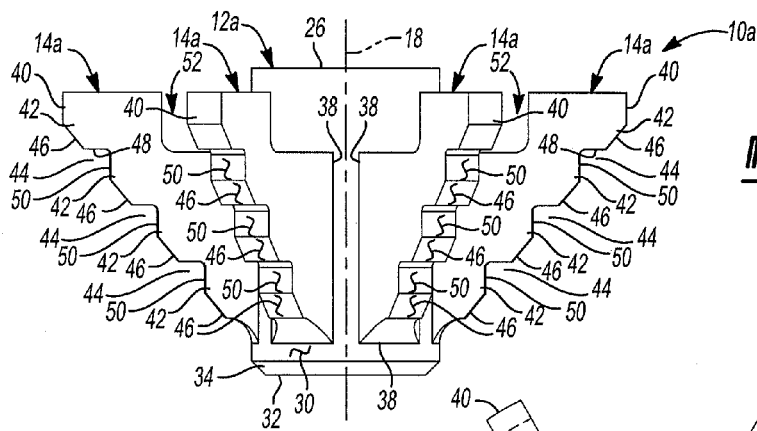
FIG. 4 is a side view of a humeral component of a shoulder prosthesis in accordance with the principles of the present disclosure.
Figure 5:
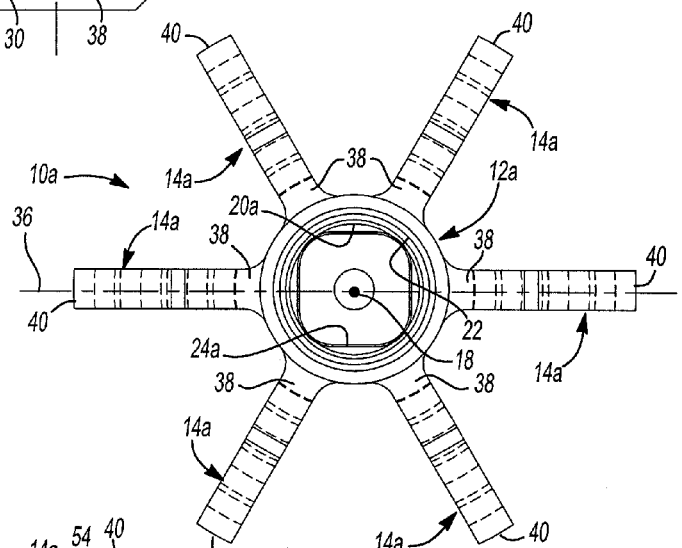
FIG. 5 is a top view of the humeral component of FIG. 4.
Figure 6:
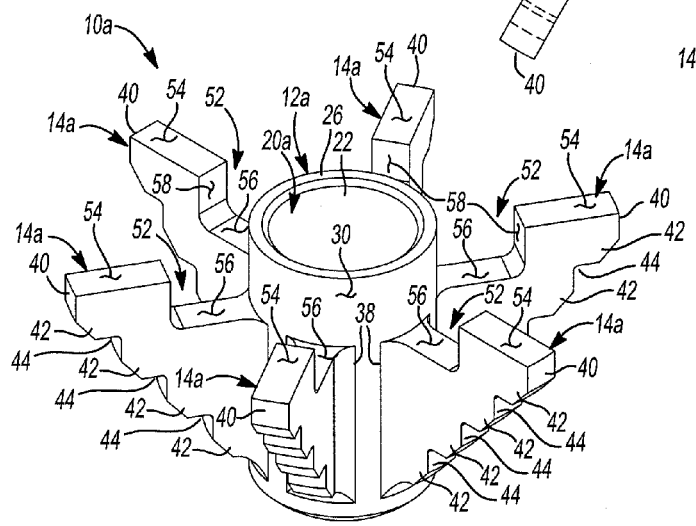
FIG. 6 is a perspective view of the humeral component of FIG. 4.
Figure 7:
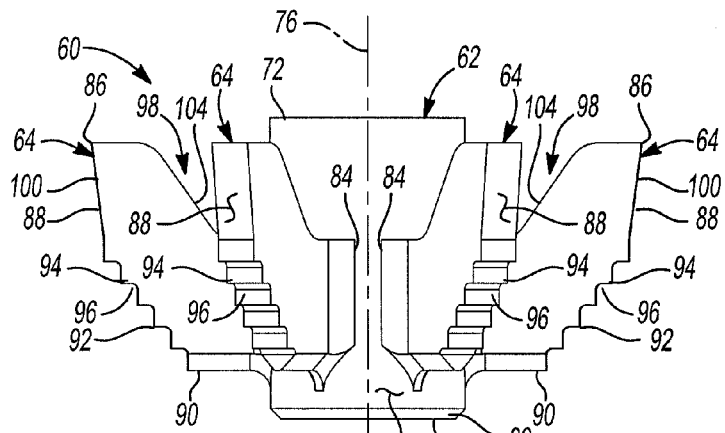
FIG. 7 is a side view of a humeral component of a shoulder prosthesis in accordance with the principles of the present disclosure.

With particular reference to FIGS. 4-6, a prosthesis 10a is shown to include a central body 12a and a plurality of wings or arms 14a. In view of the substantial similarity in structure and function of the components associated with the prosthesis 10 with respect to the prosthesis 10a, like reference numerals are used hereinafter and in the drawings to identify like components while like reference numerals containing letter extensions are used to identify those components that have been modified.

The central body 12a may include a bore 20a extending at least partially therethrough and along a longitudinal axis 18 of the central body 12a. The bore 20a may include a first portion 22 and a second portion 24a. The bore 20 may extend completely through the central body 12a or, alternatively, may be a blind bore that extends only partially through the central body 12a. Regardless of the particular construction of the bore 20a, the first portion 22 is in fluid communication with the second portion 24a such that the second portion 24a is accessed via the first portion 22 and opening 26 of the central body 12a.

The second portion 24a is disposed generally adjacent to the first portion 22 and may include a substantially square shape. The shape of the second portion 24a may be designed to matingly receive a tool (FIG. 27) during installation of the prosthesis 10a to prevent relative rotational movement between the prosthesis 10a and the tool at the second portion 24a. While the second portion 24a is shown as including a substantially square shape, the second portion 24a could include virtually any shape that permits the second portion 24a of the bore 20 to matingly receive a tool therein.

The arms 14a extend generally from the central body 12 in a direction substantially perpendicular to the longitudinal axis 18 of the central body 12a. As with the prosthesis 10, the plurality of arms 14a may include six arms 14a, whereby a line 36 bisecting the central body 12a and passing through the longitudinal axis 18 likewise passes through a pair of the arms 14a. Because the plurality of arms 14a are shown to include six arms, three such lines 36 could be constructed. Each arm 14a may include a first end 38 disposed at a junction of the central body 12a and each arm 14a as well as a second end 40. Further, each arm 14 may include a series of alternating peaks 42 and valleys 44 at the second end 40, as shown in FIGS. 4 and 6.

The arms 14a may additionally include a recess 52 that extends generally between the outer surface 30 and the second end 40 of each arm 14a. The recess 52 may be defined by a first planar surface 54 and a second planar surface 56 that are each substantially perpendicular to the longitudinal axis 18, are substantially parallel to one another, and extend in different planes. A substantially vertical surface 58 may extend generally between and connect the first planar surface 54 and the second planar surface 56 and may be substantially parallel to the longitudinal axis 18 of the central body 12a. The recess 52 allows for bone to grow over the top of each arm 14a and for placement of bone graft to help facilitate bone growth, which may allow for enhanced stability.

With particular reference to FIGS. 7-10, a prosthesis 60 is provided and may include a central body 62 and a plurality of wings or arms 64. As with the prosthetics 10, 10a, the prosthesis 60 may be received within a resected portion of a humerus during a partial or total shoulder arthroplasty. The prosthesis 60 provides a structure for receiving and supporting a prosthetic humeral head 16 once the prosthesis 60 is installed in the resected portion of the humerus.

Figure 8:
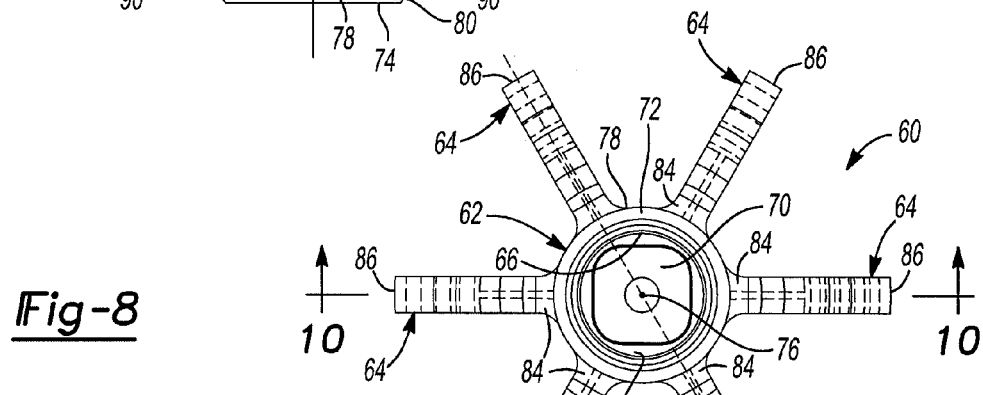
FIG. 8 is a top view of the humeral component of FIG. 7.

The central body 62 may include a bore 66 having a first portion 68 and a second portion 70. The first portion 68 may include a Morse taper and may extend generally between a first end 72 of the central body 62 and the second portion 70. The second portion 70 may be disposed adjacent to the first portion 68 and may extend generally between the first portion 68 and a second end 74 of the central body 62. The second portion 70 may include a substantially square shape, as shown in FIG. 8, to matingly receive a tool (not shown) during installation of the prosthesis 60 into a resected portion of a humerus. Interaction between the tool and the second portion 70 restricts relative rotation between the prosthesis 60 and the tool at the second portion 70 during installation of the prosthesis 60 into the humerus. While the second portion 70 is described and shown as including a substantially square shape, the second portion 70 could include any shape that permits mating engagement with a tool during installation of the prosthesis 60 to restrict relative rotation between the prosthesis 60 and the tool. Further, while the second portion 70 is described as matingly receiving the tool to restrict relative rotation therebetween, some rotation between the second portion 70 and the tool may be permitted.

The bore 66 may extend completely through the central body 62 along a longitudinal axis 76 of the central body 62. While the bore 66 is described and shown as extending completely through the central body 62 along the longitudinal axis 76, the bore 66 could alternatively be a blind bore that only partially extends through the central body 62.

Figure 9:
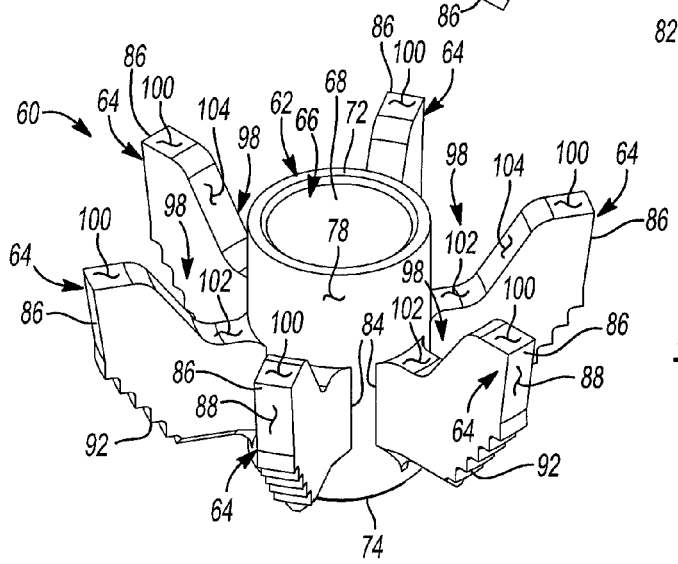
FIG. 9 is a perspective view of the humeral component of FIG. 7.

The central body 62 may additionally include a substantially uniform outer surface 78 as well as a chamfer 80 that facilitates insertion of the central body 62 into a resected portion of a humerus during installation of the prosthesis 60. The outer surface 78 of the central body 62 may provide the central body 62 with a substantially constant, cylindrical shape extending along a length of the central body 62, as shown in FIG. 9.

The arms 64 extend generally from the central body 62 in a direction substantially perpendicular to the longitudinal axis 76. The plurality of arms 64 may include six arms 64, whereby an imaginary line 82 bisecting the central body 62 passes through a pair of arms 64 (FIG. 8). Because the plurality of arms 64 is shown as including six arms 64, three such lines 82 could be constructed.

Each arm 64 may include a proximal end 84 and a distal end 86. The proximal end 84 may be located at a junction of each arm 64 and the central body 62 and may provide each arm 64 with an increased width at the junction. Providing each arm 64 with an area of increased width at the junction of the central body 62 and each arm 64 strengthens the connection of the arms 64 to the central body 62 by increasing the material located at the junction of the central body 62 and the arms 64.

Figures 10, 11:
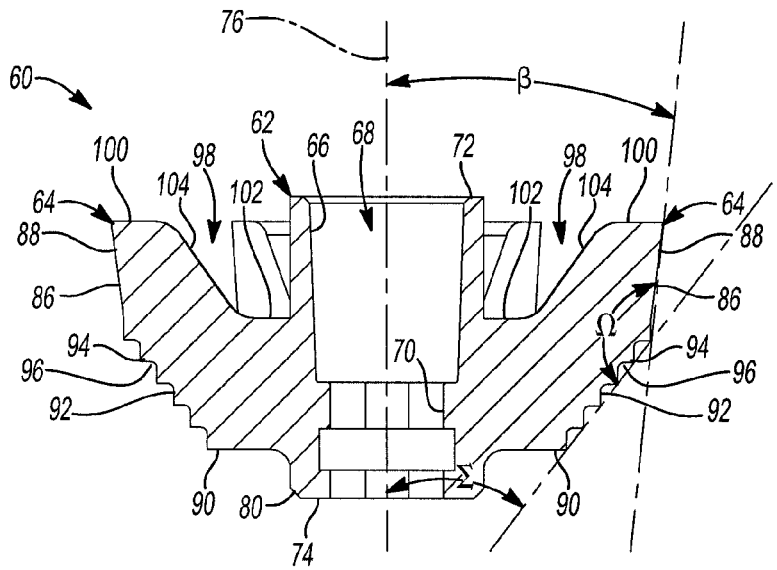
FIG. 10 is a cross-sectional view of the humeral component of FIG. 7 taken along line 10-10 of FIG. 8.
FIG. 11 is a side view of a humeral component of a shoulder prosthesis in accordance with the principles of the present disclosure.

The distal end 86 of each arm 64 may include a first surface 88, a second surface 90, and a third surface 92. The first surface 88 may be formed at an acute angle ($\beta$) relative to the longitudinal axis 76 of the central body 62 (FIG. 10). The second surface 90 may extend from the central body 62 in a direction substantially perpendicular to the longitudinal axis 76 and may be located proximate to the second end 74 of the central body 62. The third surface 92 may extend generally between the first surface 88 and the second surface 90 and may include a series of peaks 94 and valleys 96. An imaginary line connecting the peaks 94 may be formed at an obtuse angle ($\Omega$) relative to the first surface (88) and may be formed at an acute angle ($\Sigma$) relative to the longitudinal axis (76).

The arms 64 may additionally include a recess 98 disposed generally between the distal end 86 of each arm 64 and the outer surface 78 of the central body 62. The recess 98 may be defined generally by a first planar surface 100, a second planar surface 102, and a surface 104. The first planar surface 100 and the second planar surface 102 extend generally from the central body 62 in a direction substantially perpendicular to the longitudinal axis 76. The first planar surface 100 and the second planar surface 102 may be substantially parallel to one another and may be located in different planes such that the first planar surface 100 is located closer to the first end 72 of the central body 62 and the second planar surface 102 is located closer to the second end 74 of the central body 62, as shown in FIG. 10. The surface 104 extends between the first planar surface 100 and the second planar surface 102 to connect the first planar surface 100 and the second planar surface 102. The surface 104 may be planar and may be connected to surfaces 100 and 102 by radii. The first planar surface 100, second planar surface 102, and surface 104 cooperate with the outer surface 78 of the central body 62 to define the recess 98 of each arm 64.

Figure 12:
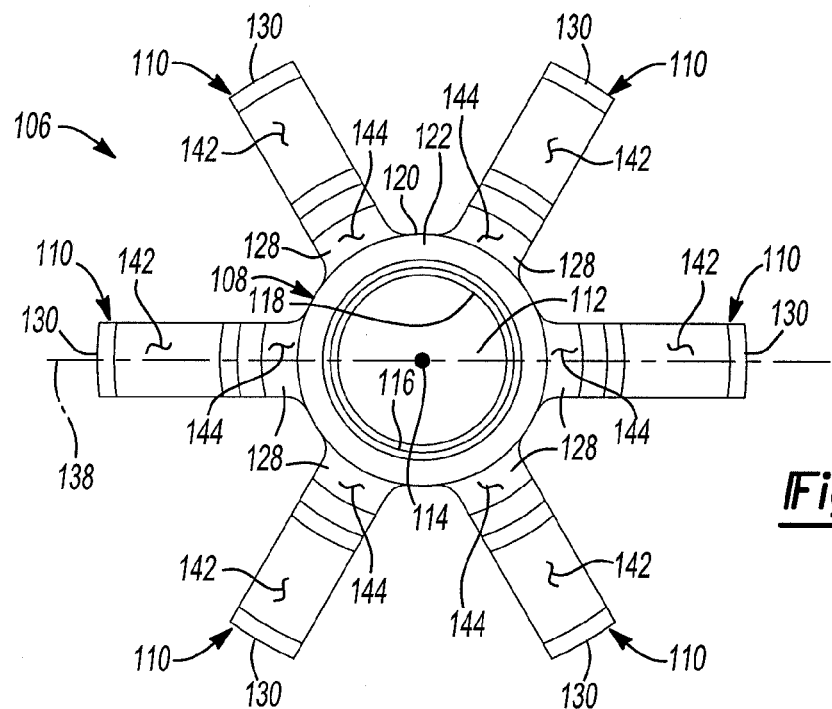
FIG. 12 is a top view of the humeral component of FIG. 11.
Figure 13:
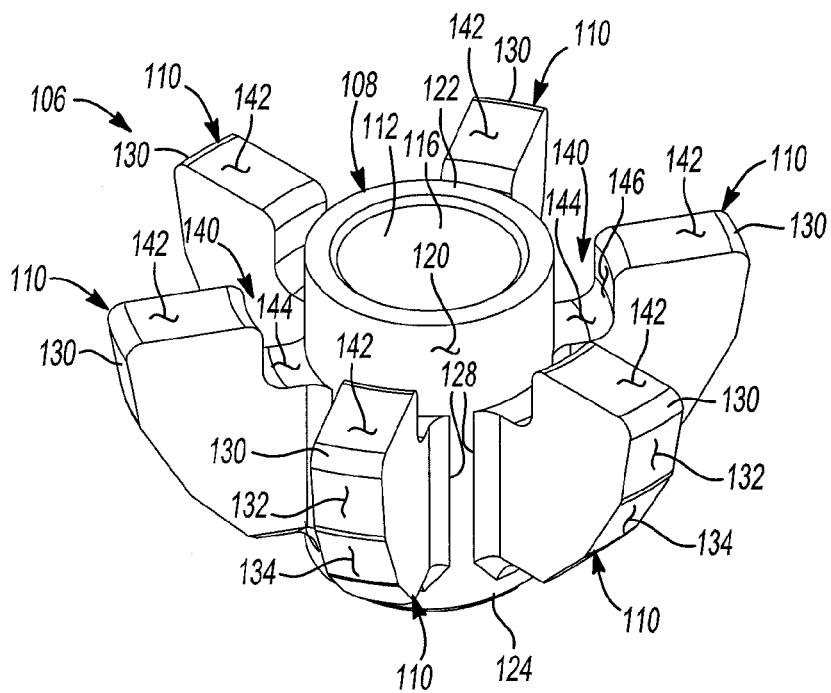
FIG. 13 is a perspective view of the humeral component of FIG. 11.

With particular reference to FIGS. 11-13, a prosthesis 106 is shown to include a central body 108 and a plurality of wings or arms 110. As with the prosthetics 10, 10a, 60, the prosthesis 106 may be used during a partial or total shoulder arthroplasty and may be received within a resected portion of a humerus. The prosthesis 106 may provide a structure on which a prosthetic humeral head 16 may be supported relative to the resected portion of the humerus.

The central body 108 may include a substantially circular shape and may include a bore 112 at least partially formed therethrough and extending along a longitudinal axis 114 of the central body 108. The bore 112 may include a first portion 116 and a second portion 118. The bore 112 may extend completely through the central body 108 or, alternatively, the bore 112 may be a blind bore extending only partially through the central body 108. Regardless of the particular construction of the bore 112, the first portion 116 may include a Morse taper for receiving a portion of the prosthetic humeral head 16.

The second portion 118 may include a series of threads (not shown) or, alternatively, a shape for mating engagement with a tool (FIG. 27). The tool may matingly engage the second portion 118 to facilitate attachment between the tool and the central body 108 of the prosthesis 106 during installation of the prosthesis 106 into the resected portion of the humerus during a partial or total shoulder arthroplasty. Engagement between the tool and the second portion 118 of the central body 108 inhibits relative rotation between the tool and the central body 108 during installation of the prosthesis 106 and, as a result, enhances the ability of the tool to engage and position the prosthesis 106 within the resected portion of the humerus.

The central body 108 may additionally include an outer surface 120 that defines the substantially cylindrical shape of the central body 108. The outer surface 120 may extend between a first end 122 and a second end 124 (FIG. 11). The second end 124 may include a chamfer 126 to facilitate insertion of the central body 108 into the resected portion of the humerus.

With continued reference to FIGS. 11-13, the arms 110 are shown as including a first end 128 and a second end 130. The first end 128 may include an increased thickness at a junction of the central body 108 and each arm 110 to increase the overall contact area between the central body 108 and each arm 110. Increasing the thickness of each arm 110 at the first end 128 increases the strength of the arms 110 at the central body 108 and, as a result, improves the overall strength of the prosthesis 106.

The second end 130 is formed on an opposite end of each arm 110 from the first end 128 and may include a first planar surface 132, a second planar surface 134, and a third planar surface 136. The first planar surface 132, second planar surface 134, and third planar surface 136 may all be formed at an acute angle relative to the longitudinal axis 114 of the central body 108. For example, the first planar surface 132 may be formed at an acute angle ($\theta$) relative to the longitudinal axis 114, the second planar surface 134 may be formed at an acute angle ($\psi$), and the third planar surface 136 may be formed at an acute angle ($\phi$) relative to the longitudinal axis 114. In addition, the first planar surface 132, second planar surface 134, and third planar surface 136 may be formed at an obtuse angle relative to one another. For example, the third planar surface 136 may be formed at an obtuse angle ($\delta$) relative to the second planar surface 134. Likewise, the second planar surface 134 may be formed at an obtuse angle ($\alpha$) relative to the first planar surface 132.

The arms 110 may extend from the central body 108 in a direction substantially perpendicular to the longitudinal axis 114 of the central body 108. As such, an imaginary line 138 passing through the longitudinal axis 114 and bisecting the central body 108 likewise passes through a pair of the arms 110, as shown in FIG. 12. Because the plurality of arms 110 is shown to include six arms, three such lines 138 could be constructed.

The arms 110 may include a recess 140 extending generally between the outer surface 120 of the central body 108 and the second end 130 of each arm 110. The recess 140 may be defined generally by a first planar surface 142, a second planar surface 144, and a third planar surface 146. The first planar surface 142 and the second planar surface 144 may extend generally from the central body 108 in a direction substantially perpendicular to the longitudinal axis 114. The first planar surface 142 may be substantially parallel to the second planar surface 144, whereby the first planar surface 142 and the second planar surface 144 extend in different planes.

As described, the first planar surface 142 is disposed closer to the first end 122 of the central body 108 and the second planar surface 144 is disposed closer to the second end 124 of the central body 108. The third planar surface 146 is disposed generally between the first planar surface 142 and the second planar surface 144 and may be formed substantially parallel to the longitudinal axis 114 of the central body 108. As such, the third planar surface 146 may be substantially parallel to the outer surface 120 of the central body 108 to define the recesses 140 of the arms 110.

The foregoing prosthetics 10, 10a, 60, 106 may be formed from any suitable biocompatible material. For example, the prosthetics 10, 10a, 60, 106 may be formed from a titanium alloy (e.g., Ti-6Al-4V), CoCrMo, Pyrocarbon, or PEEK. In addition, the central bodies 12, 12a, 62, 108 and/or arms 14, 14a, 64, 110 may be coated with a porous plasma spray (PPS), Regenerex, or Hydroxy Apatite (HA), or any other appropriate coating that promotes boney ingrowth or ongrowth. Providing the various prosthetics 10, 10a, 60, 106 with such a coating to promote boney ingrowth or ongrowth helps ensure that the prosthesis 10, 10a, 60, 106 is retained at a desired position within the resected humerus by encouraging boney ingrowth and/or ongrowth that helps retain the prosthetics 10, 10a, 60, 106 at the desired position relative to the humerus.

The prosthetics 10, 10a, 60, 106 may be formed from a traditional manufacturing method such as, for example, machining or forging. Alternatively, the prosthetics 10, 10a, 60, 106 may be formed from an additive manufacturing process such as Electron Beam Melting (EBM) or Direct Metal Laser Sintering (DMLS). If the prosthetics 10, 10a, 60, 106 are formed from an additive manufacturing process, the prosthetics 10, 10a, 60, 106 may be machined thereafter to form the Morse taper and inserter mating features within the bores 20, 20a, 66, 112 of the respective prosthetics 10, 10a, 60, 106.

Utilizing an additive manufacturing process allows the prosthetics 10, 10a, 60, 106 to be formed in a substantially net shape and may provide each prosthesis 10, 10a, 60, 106 with a substantially mesh or porous structure. Furthermore, manufacturing the prosthetics 10, 10a, 60, 106 via an additive manufacturing process allows the prosthetics 10, 10a, 60, 106 to include areas of solid material adjacent to or embedded within the porous structure of the prosthesis 10, 10a, 60, 106.

With particular reference to FIGS. 14-22, various configurations of the prosthesis 106 are provided, whereby the prosthesis 106 is formed via an additive manufacturing process. FIGS. 14-21 depict at least a portion of the central body 108 and arms 110 as being formed from a porous material, whereby the central body 108 and/or arms 110 include pores formed in between biomaterial. While the prosthesis 106 is described and shown as being formed from an additive manufacturing process and as including a mesh or porous material at the central body 108 and/or arms 110, any of the prosthetics 10, 10a, 60 could be formed via an additive manufacturing process to include a mesh or porous material.

Figure 14:
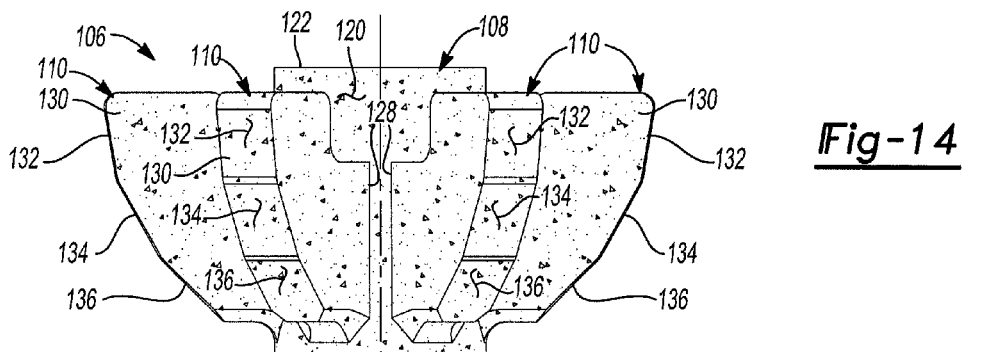
FIG. 14 is a side view of a humeral component of a shoulder prosthesis in accordance with the principles of the present disclosure.
Figure 15:
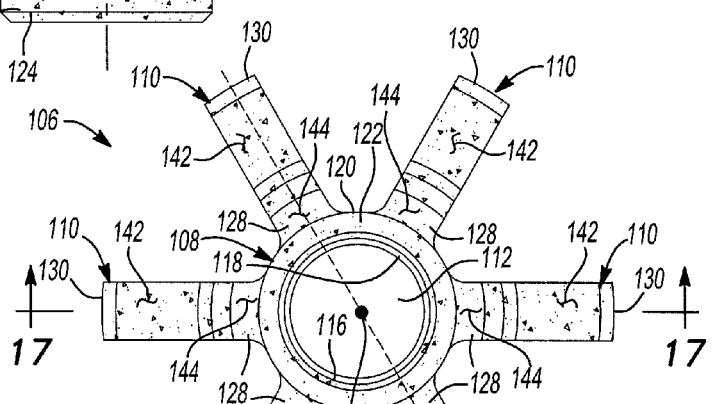
FIG. 15 is a top view of the humeral component of FIG. 14.
Figure 16:
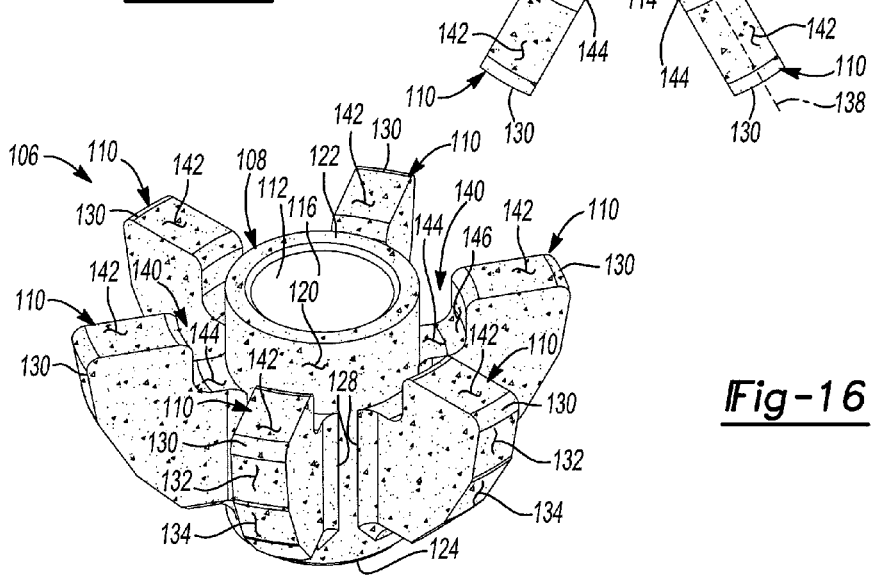
FIG. 16 is a perspective view of the humeral component of FIG. 14.

FIGS. 14-16 generally depict the prosthesis 106 as including a porous material that forms a portion of the central body 108 and at least a portion of the arms 110. For example, the cross-sectional view of FIG. 17 identifies a portion of the central body 108 and arms 110 as being formed from a porous material. Forming a portion of the central body 108 from a porous material allows the central body 108 to be machined. For example, the central portion 108 may be machined to include a taper to allow the central portion 108 to properly receive an installation tool and subsequently a portion of a humeral head 16.

The arms 110 are shown as including a solid portion 148 disposed generally within the arms 110 and connected to the central portion 108. The solid portion 148 may be configured such that the solid portion 148 mimics the outer profile of each arm 110, whereby the solid portion 148 similarly includes a first surface 150, a second surface 152, and a third surface 154. Namely, the first surface 150, second surface 152, and third surface 154 are respectively disposed adjacent and parallel to surfaces 132, 134, and 136 of each arm 110. In addition, the solid portion 148 may include a fourth surface 156 that is substantially parallel to the first planar surface 142 and a fifth surface 158 that is substantially parallel to the outer surface 120 of the central body 108.

Figure 17:
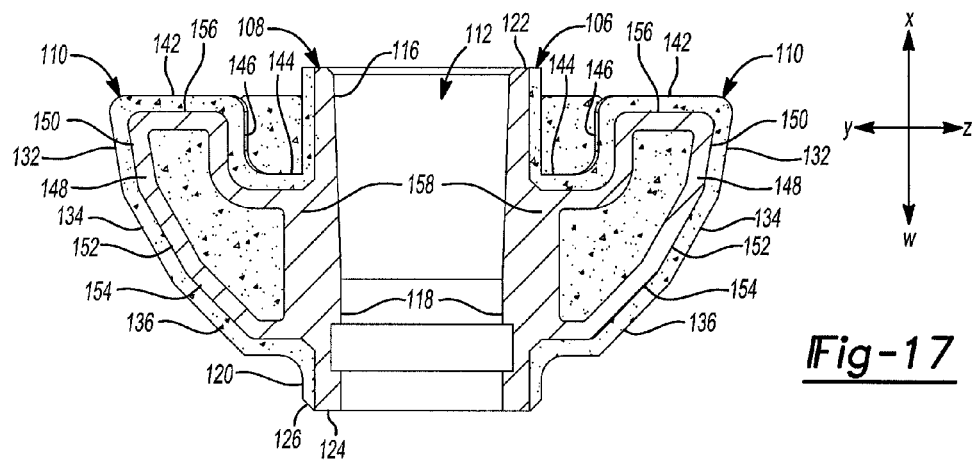
FIG. 17 is a cross-sectional view of the humeral component of FIG. 14 taken along line 17-17 of FIG. 15.

The solid portion 148 may be surrounded by a porous material and may be positioned within the arms 110 at virtually any location and may include virtually any shape to provide each arm 110 with additional strength. During manufacturing of the prosthesis 106, the porous material, as well as the solid portion 148, may be formed by depositing layer upon layer until the shape of the prosthesis 106 shown in FIG. 17 is obtained. For example, the layers may be added to one another in any of the (W), (X), (Y), and (Z) directions during manufacturing (FIG. 17).

Figure 18:
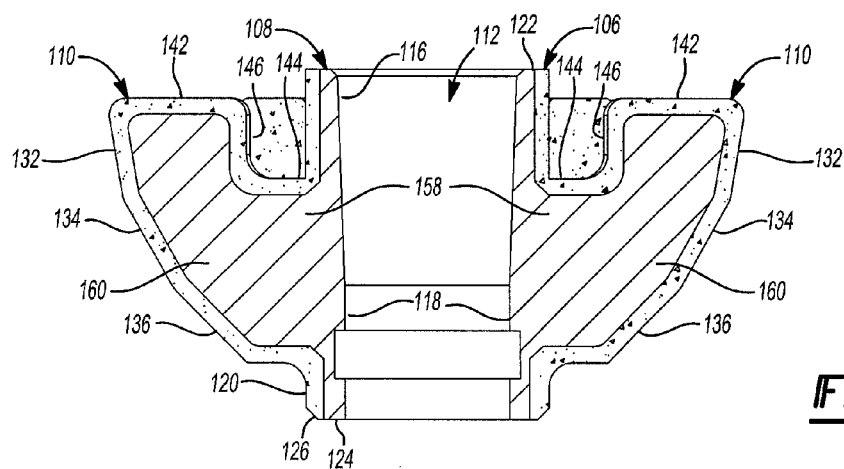
FIG. 18 is a cross-sectional view of the shoulder prosthesis of FIG. 14 taken along line 17-17 of FIG. 15 and including an alternate arm construction.

With particular reference to FIG. 18, the prosthesis 106 is shown to include a solid portion 160 having a similar shape to that of the solid portion 148. While the solid portion 160 includes a substantially similar shape as the solid portion 148, the solid portion 160 of FIG. 18 includes additional solid material when compared to the solid portion 148 of FIG. 17. Providing the prosthesis 106 with additional solid material, as shown in FIG. 18, additionally strengthens the arms 110 and, thus, strengthens the overall prosthesis 106.

Figure 19:
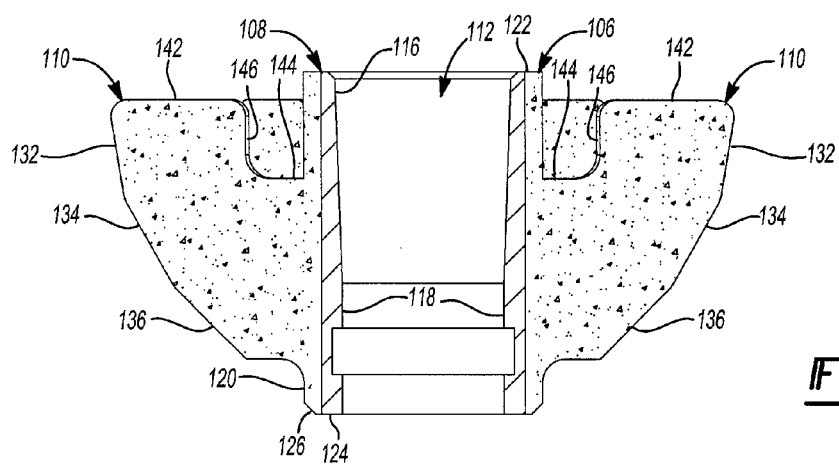
FIG. 19 is a cross-sectional view of the humeral component of FIG. 14 taken along line 17-17 of FIG. 15 and including an alternate arm construction.

With particular reference to FIG. 19, the prosthesis 106 is shown as being formed entirely from a porous material, except for a portion of the central body 108 to allow the central portion 108 to be machined. In this configuration, the central body 108 and arms 110 are completely formed from a porous material and do not include a solid portion, as shown in FIGS. 17 and 18.

Figure 20:
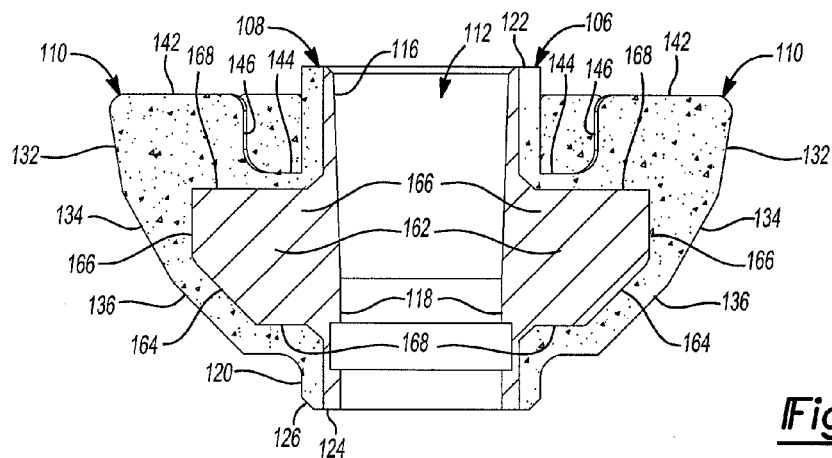
FIG. 20 is a cross-sectional view of the humeral component of FIG. 14 taken along line 17-17 of FIG. 15 and including an alternate arm construction.

With particular reference to FIG. 20, the prosthesis 106 is shown as including a solid portion 162 having a different configuration than the solid portions 148, 160 of FIGS. 17 and 18, respectively. The solid portion 162 includes a first surface 164 that is substantially parallel to the third planar surface 136, as well as a pair of planar surfaces 166 that are substantially parallel to the longitudinal axis 114 of the central body 108. Additionally, the solid portion 162 may include a pair of planar surfaces 168 that are substantially perpendicular to the longitudinal axis 114 of the central body 108.

Figure 21:
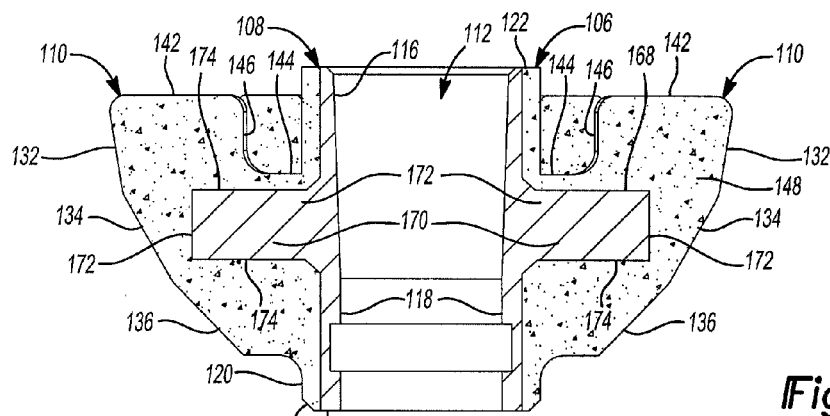
FIG. 21 is a cross-sectional view of the humeral component of FIG. 14 taken along line 17-17 of FIG. 15 and including an alternate arm construction.

With particular reference to FIG. 21, the prosthesis 106 is shown as including a solid portion 170 having a pair of planar surfaces 172 that are substantially parallel to the longitudinal axis 114 of the central body 108 and a pair of planar surfaces 174 that are substantially perpendicular to the longitudinal axis 114 of the central body 108. As with the solid portions 148, 160, 162, the solid portion 170 adds to the overall strength of the prosthesis 106 by extending into the arms 110 in an effort to strengthen the arms 110 proximate to a junction of the central body 108 and the arms 110.

Figure 22:
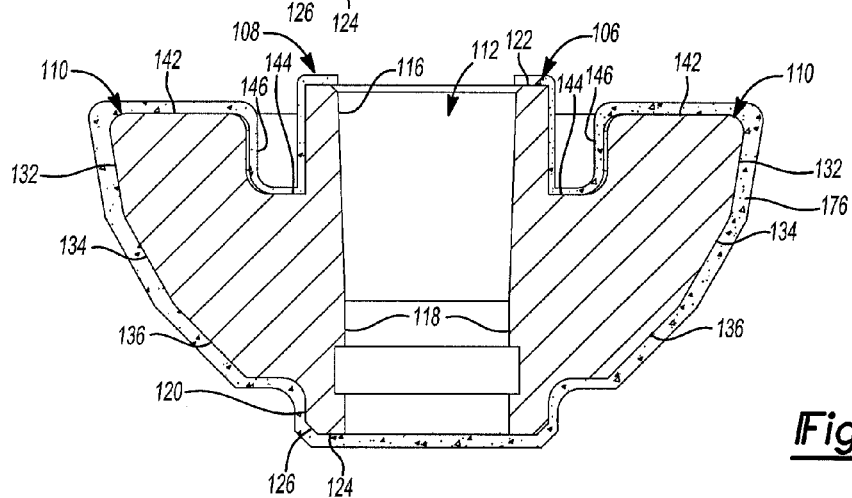
FIG. 22 is a cross-sectional view of the humeral component of FIG. 14 taken along line 17-17 of FIG. 15 and including an alternate arm construction.

With particular reference to FIG. 22, the prosthesis is shown without having any regions of porous material. As such, the prosthesis 106 shown in FIG. 22 is entirely solid and therefore may be coated with a coating 176 that promotes boney ingrowth or ongrowth once installed in the humerus.

With particular reference to FIGS. 23-27, installation of the prosthesis 10 will be described in detail. While the following installation will be described with respect to the prosthesis 10, the following installation could be performed with any of the prosthetics 10, 10a, 60, 106.

During a partial or total shoulder arthroplasty, a surgeon first makes an incision proximate to the shoulder joint of the patient to expose the humerus and glenoid fossa. Once exposed, the surgeon may use a template (not shown) to make a resection of the humerus 178 along line 180 of FIG. 25. Once the humerus 178 is resected, the surgeon may then use a tool such as a central pin and reamer/broach (none shown) to prepare a proximal end of the humerus 178 to allow the humerus 178 to receive the prosthesis 10. In one configuration, the reamer/broach creates a central pocket for receiving the central body 12 as well as a series of recesses extending from the central body 12 in spaced relation to one another in an effort to matingly receive the arms 14 once the prosthesis 10 is inserted into the humerus 178.

Prior to inserting the prosthesis 10 into the humerus 178, a suitable adhesive and/or coating may be applied to both retain the prosthesis 10 within the humerus 178 and to promote boney ingrowth and/or ongrowth. If the prosthesis 10 includes a recess such as recesses 52 of prosthesis 10a, recess 98 of prosthesis 60, or recess 140 of prosthesis 106, a bone graft material may additionally be applied therein to further retain the prosthesis 10 within the humerus 178 and to promote bone growth over and within the recesses 52, 98, 140.

Once the prosthesis 10 is positioned relative to the humerus 178, a tool may be received within the bore 20 and may threadably engage the threads 28 of the second portion 28 of the bore 20 (FIG. 27). A force may be applied to the tool in the direction (Z) shown in FIG. 27 to drive the prosthesis 10 into the humerus 178 until the prosthesis 10 is positioned in a desired position relative to the humerus 178.

Once the prosthesis 10 is disposed within the humerus 178, a tool 182 may be used to position the prosthetic humeral head 16 relative to the prosthesis 10 such that a portion of the prosthetic humeral head 16 is received within the bore 20 of the prosthesis 10. Specifically, the prosthetic humeral head 16 may include an extension 184 having a Morse taper. The extension 184 may include a male Morse taper while the first portion 22 of the bore 20 includes a mating female Morse taper such that when the extension 184 is received within the bore 20 of the central body 12, the prosthetic humeral head 16 is retained by the prosthesis 10 and held in a desired position relative to the humerus 178.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A prosthesis comprising:
a central body having a longitudinal axis; and
a plurality of arms extending from said central body in a direction substantially perpendicular to said longitudinal axis, said plurality of arms each including a first planar surface, a second planar surface, and a third planar surface that are each formed at an obtuse angle relative to one another to define an outer shape of the prosthesis, a fourth surface joining said first planar surface to said central body, and a fifth surface joining said third planar surface to said central body.

2. The prosthesis of claim 1, wherein each of said first planar surface, said second planar surface, and said third planar surface are formed at a different acute angle relative to said longitudinal axis.

3. The prosthesis of claim 1, wherein said first planar surface, said second planar surface, and said third planar surface define a width of said plurality of arms.

4. The prosthesis of claim 1, wherein said second planar surface is disposed between said first planar surface and said third planar surface.

5. The prosthesis of claim 1, wherein at least a portion of said fourth surface and a portion of said fifth surface is planar and extends away from said central body in a direction substantially perpendicular to said longitudinal axis.

6. The prosthesis of claim 1, wherein said central body includes a bore having at least one of a threaded portion and a Morse taper.

7. The prosthesis of claim 1, wherein said plurality of arms are formed from a porous material.

8. A prosthesis comprising:
a central body having a longitudinal axis; and
a plurality of arms extending from said central body in a direction substantially perpendicular to said longitudinal axis, said plurality of arms each including a first planar surface, a second planar surface, and a third planar surface that are each formed at an obtuse angle relative to one another and at an acute angle relative to said longitudinal axis to define an outer shape of the prosthesis, a fourth surface joining said first planar surface to said central body, and a fifth surface joining said third planar surface to said central body.

9. The prosthesis of claim 8, wherein each of said first planar surface, said second planar surface, and said third planar surface are formed at different angles relative to said longitudinal axis.

10. The prosthesis of claim 8, wherein said first planar surface, said second planar surface, and said third planar surface span a width of said plurality of arms.

11. The prosthesis of claim 8, wherein said second planar surface is disposed between said first planar surface and said third planar surface.

12. The prosthesis of claim 8, wherein at least a portion of said fourth surface and a portion of said fifth surface is planar and extends away from said central body in a direction substantially perpendicular to said longitudinal axis.

13. The prosthesis of claim 8, wherein said central body includes a bore having at least one of a threaded portion and a Morse taper.

14. The prosthesis of claim 8, wherein said plurality of arms are formed from a porous material.

* * * * *

UNITED STATES PATENT AND TRADEMARK OFFICE
CERTIFICATE OF CORRECTION

PATENT NO. : 8,506,638 B2  
APPLICATION NO. : 13/182026  
DATED : August 13, 2013  
INVENTOR(S) : Thomas M. Vanasse and Nathan A. Winslow Page 1 of 1

It is certified that error appears in the above-identified patent and that said Letters Patent is hereby corrected as shown below:

Title Page, Col. 1, item (73) Assignee, Line 1, Delete "Biomets" and insert --Biomet--  
Title Page 2, Col. 2, item (56) Other Publications, Line 5, Delete "S.T.," and insert --S. T.,--  
Title Page 2, Col. 2, item (56) Other Publications, Line 5, Delete "V.N.." and insert --V. N.,--  
Title Page 2, Col. 2, item (56) Other Publications, Line 9, Delete "D.M.." and insert --D. M.,--  
Title Page 2, Col. 2, item (56) Other Publications, Line 13, Delete "G.A.." and insert --G. A.,--  
Title Page 2, Col. 2, item (56) Other Publications, Line 19, Delete "G.A." and insert --G. A.,--  
Title Page 2, Col. 2, item (56) Other Publications, Line 21, Delete "ortopedir" and insert --ortopedii--  
Title Page 2, Col. 2, item (56) Other Publications, Line 22, Delete "N.N." and insert --N. N.--  
Title Page 2, Col. 2, item (56) Other Publications, Line 23, Delete "N.N." and insert --N. N.--  
Title Page 2, Col. 2, item (56) Other Publications, Line 24, Delete "Sh.Sh.," and insert --Sh. Sh.,--  
Title Page 2, Col. 2, item (56) Other Publications, Line 26, Delete "N.N." and insert --N. N.--  
Title Page 2, Col. 2, item (56) Other Publications, Line 27, Delete "n. N." and insert --N. N.--  
Title Page 2, Col. 2, item (56) Other Publications, Line 29, Delete "A.I.," and insert --A. I.,--  
Title Page 2, Col. 2, item (56) Other Publications, Line 34, Delete "O" and insert --O.--  
Title Page 2, Col. 2, item (56) Other Publications, Line 35, Delete "S.A." and insert --S. A.--

In the Specification  
Col. 6, Line 3, Delete "20" and insert --20a--  
Col. 6, Line 4, Delete "12" and insert --12a--  
Col. 6, Line 6, Delete "10" and insert --10a--  
Col. 6, Line 14, Delete "14" and insert --14a--

Signed and Sealed this  
Fifth Day of November, 2013

Teresa Stanek Rea  
*Deputy Director of the United States Patent and Trademark Office*